(12) United States Patent
Magovern

(10) Patent No.: US 6,527,796 B1
(45) Date of Patent: Mar. 4, 2003

(54) METHOD AND APPARATUS FOR BURNING CALORIES

(76) Inventor: James A. Magovern, 603 Twin Pine Rd., Pittsburgh, PA (US) 15215

( * ) Notice: Subject to any disclaimer, the term of this patent is extended or adjusted under 35 U.S.C. 154(b) by 0 days.

(21) Appl. No.: 09/490,300

(22) Filed: Jan. 24, 2000

(51) Int. Cl.$^7$ ............................................... A61H 21/00
(52) U.S. Cl. ............................ 607/81; 607/80; 607/82; 607/83
(58) Field of Search .......................... 607/96, 114, 104, 607/107, 112, 81

(56) References Cited

U.S. PATENT DOCUMENTS

| | | | | |
|---|---|---|---|---|
| 4,546,506 A | * | 10/1985 | Houle et al. .................. 4/555 |
| 4,784,140 A | * | 11/1988 | Donnerback et al. ....... 128/374 |
| 4,825,207 A | * | 4/1989 | Snell ........................... 340/3.7 |
| 5,062,424 A | * | 11/1991 | Hooker ...................... 128/897 |
| 5,183,039 A | * | 2/1993 | Sarian et al. ............... 128/400 |
| 5,433,083 A | * | 7/1995 | Kuramarohit .............. 62/259.3 |
| 5,486,208 A | * | 1/1996 | Ginsburg .................... 607/106 |
| 5,653,239 A | * | 8/1997 | Pompei et al. ............. 128/664 |
| 5,837,003 A | * | 11/1998 | Ginsburg .................... 607/106 |
| 6,128,795 A | * | 10/2000 | Stanley et al. ................ 5/421 |

* cited by examiner

Primary Examiner—Michael Peffley
Assistant Examiner—Pete J Vrettakos
(74) Attorney, Agent, or Firm—Ansel M. Schwartz

(57) ABSTRACT

An apparatus for burning calories of an individual. The apparatus includes a cooling mechanism adapted to cool the individual's temperature. The apparatus includes a controlling mechanism for controlling the rate at which the cooling mechanism cools the individual. A method for burning calories in an individual. The method includes the steps of applying a fluid in regard to the individual. Then there is the step of cooling the individual at the controlled rate with the fluid.

26 Claims, 3 Drawing Sheets

METHOD AND APPARATUS FOR BURNING CALORIES

FIELD OF THE INVENTION

The present invention is related to a method and apparatus for increased burning of calories in an individual without the individual having to exercise. More specifically, the present invention is related to a method and apparatus for increased burning of calories in an individual by causing the body temperature of the individual to drop until the individual shivers.

BACKGROUND OF THE INVENTION

A significant percentage of the population is concerned about their weight, either due to health reasons or appearance reasons, or both. An untold number of diets, devices or techniques are used by individuals to lose weight. A simple equation that is appropriate in regard to losing weight is to burn more calories than are consumed in a given day, causing the excess calories being burned to come from fat stored in the body of the individual. One simple way of doing this is eating less. Another way is to increase the way the body of the individual burns calories. In regard to the latter, many individuals would like to exercise, but for one reason or another do not exercise as they should to maintain their body weight or to lose weight.

The present invention is directed to increasing the burning of calories of an individual by causing the body temperature of the individual to drop so the individual shivers. When an individual shivers, the body is expending substantially more energy than it otherwise would, and it attains this energy by burning calories, such as from fat stored in the body.

SUMMARY OF THE INVENTION

The present invention pertains to an apparatus for burning calories of an individual. The apparatus comprises a cooling mechanism adapted to cool the individual's temperature and preferably the individual's core temperature. The apparatus comprises a controlling mechanism for controlling the rate at which the cooling mechanism cools the individual.

The present invention pertains to a method for burning calories in an individual. The method comprises the steps of applying a fluid in regard to the individual. Then there is the step of cooling the individual at the controlled rate with the fluid.

BRIEF DESCRIPTION OF THE DRAWINGS

In the accompanying drawings, the preferred embodiment of the invention and preferred methods of practicing the invention are illustrated in which.

DETAILED DESCRIPTION

Figure 1:
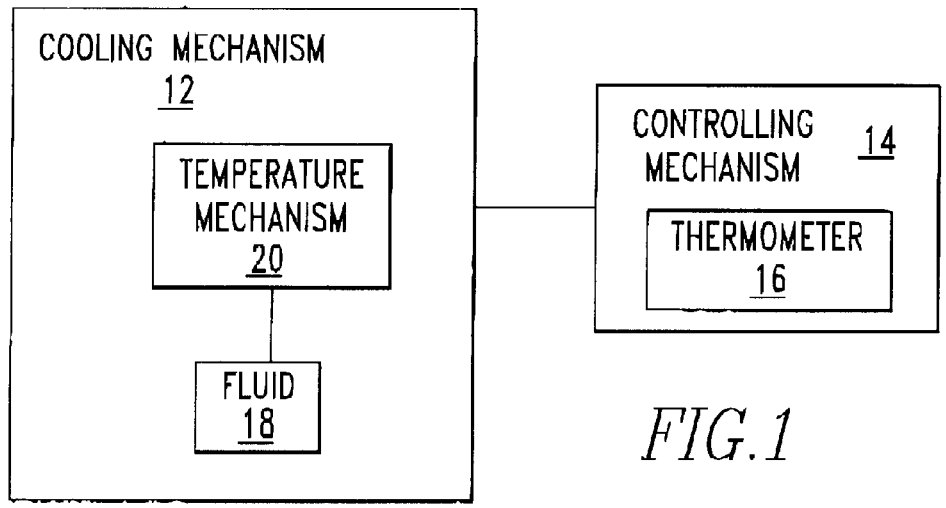
FIG. 1 is a schematic representation of an apparatus of the present invention.

Referring now to the drawings wherein like reference numerals refer to similar or identical parts throughout the several views, and more specifically to FIG. 1 thereof, there is shown an apparatus 10 for burning calories of an individual. The apparatus 10 comprises a cooling mechanism 12 adapted to cool the individual's temperature. The apparatus 10 comprises a controlling mechanism 14 for controlling the rate at which the cooling mechanism 12 cools the individual.

Preferably, the controlling mechanism 14 includes a thermometer 16 adapted to monitor the individual's temperature. Preferably, the thermometer 16 is adapted to attach to the ear of the individual. The cooling mechanism 12 preferably includes a fluid 18 for cooling the individual.

Preferably, the cooling mechanism 12 includes a temperature mechanism 20 for controlling the temperature of the fluid 18. The temperature mechanism 20 causes the fluid 18 temperature to be greater than 78 and preferably 85 degrees Fahrenheit when the fluid 18 is initially used for the individual and then gradually reduces the temperature of the fluid 18 to below 68 degrees Fahrenheit. Preferably, the temperature mechanism 20 raises the temperature of the fluid 18 so that the initial sensation is not uncomfortable, and then gradually raises the temperature of the fluid 18 to cause vasodilatation, before gradually reducing the temperature of the fluid 18 to cause cooling.

Figure 2:
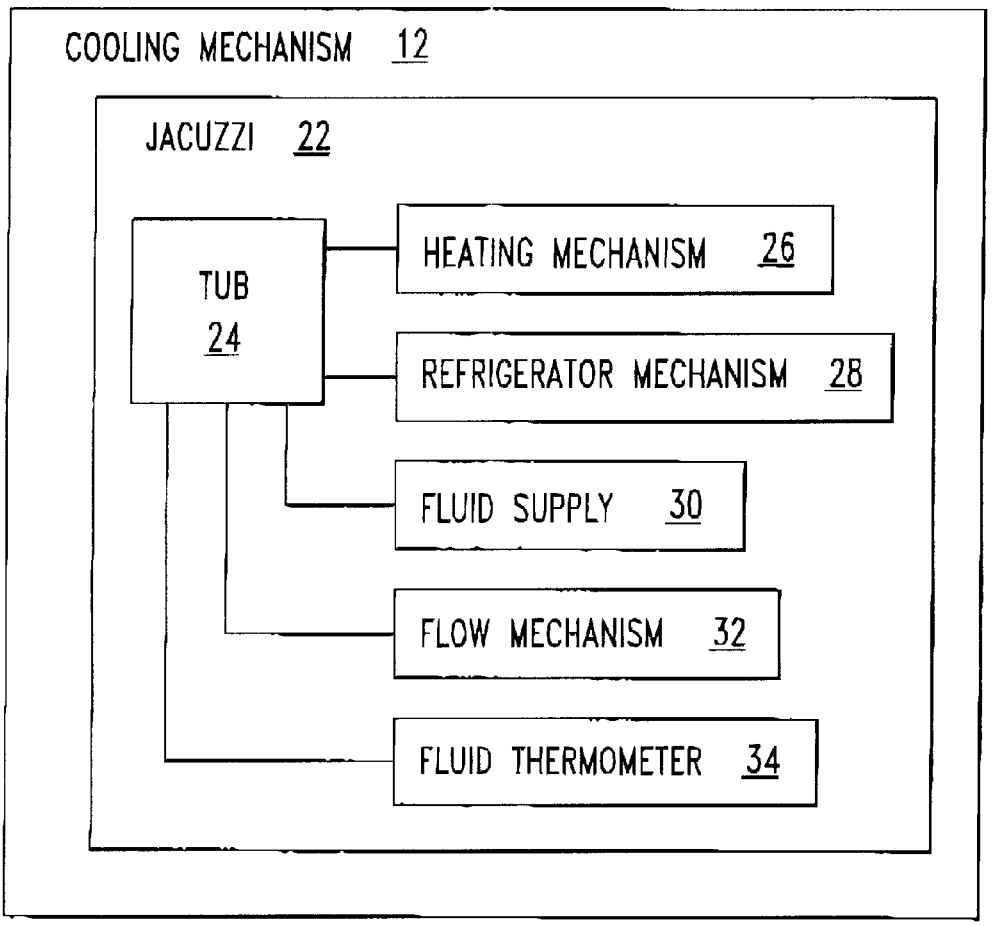
FIG. 2 is a schematic representation of a cooling mechanism with a Jacuzzi.

The cooling mechanism 12 preferably includes a Jacuzzi 22 connected to the controller mechanism, as shown in FIG. 2. The Jacuzzi 22 has a tub 24, a heating mechanism 26 for heating fluid 18, a refrigerator mechanism 28 for cooling fluid 18, a fluid 18 supply 30 for filling the tub 24, a flow mechanism 32 for moving the fluid 18 through the tub 24 and the heating mechanism 26 and the cooling mechanism 12, and a fluid thermometer 34 for measuring the temperature of the fluid 18.

Figure 3:
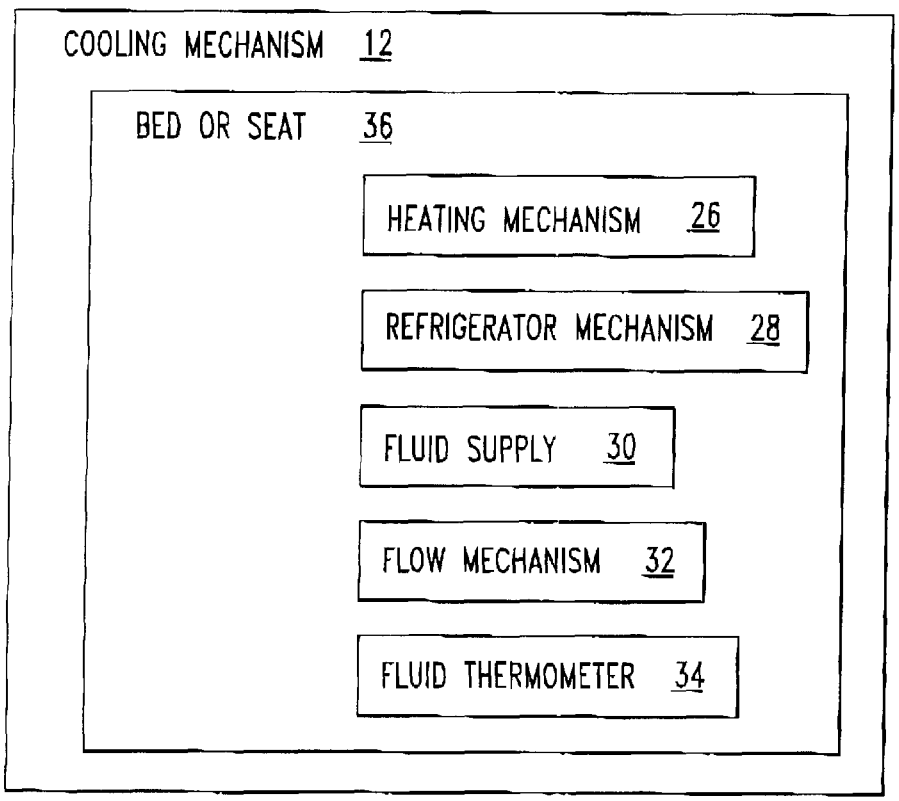
FIG. 3 is a schematic representation of a cooling mechanism with a bed or seat.
Figure 4:
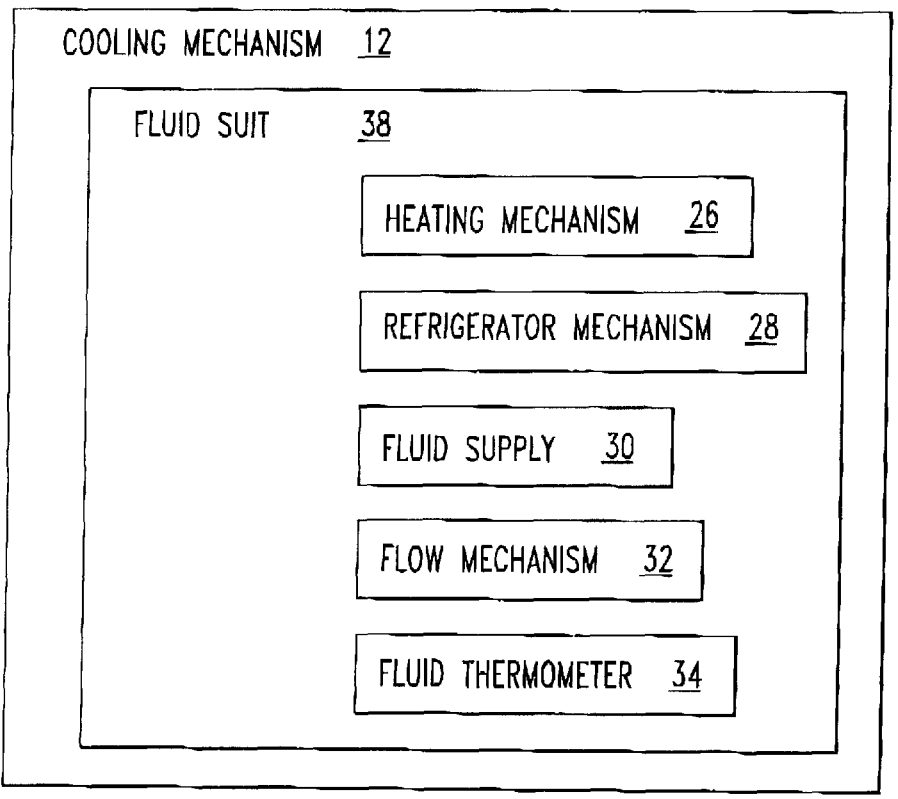
FIG. 4 is a schematic representation of a cooling mechanism with a fluid suit.
Figure 5:
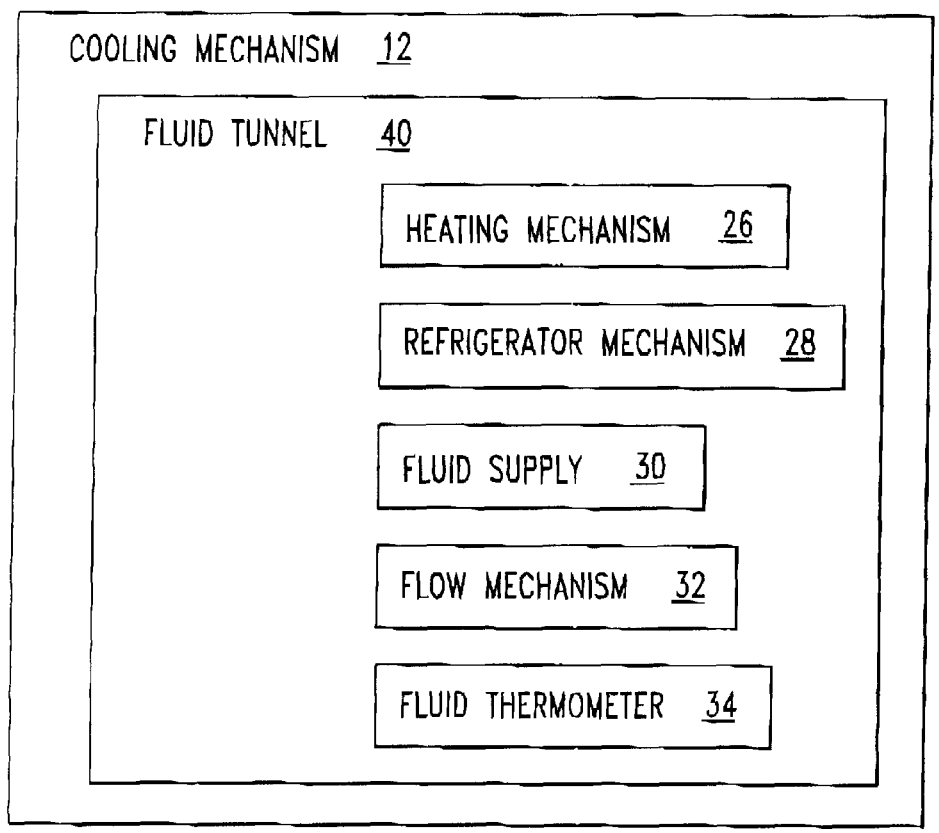
FIG. 5 is a schematic representation of the cooling mechanism with a fluid tunnel.

Alternatively, the cooling mechanism 12 includes a fluid bed or seat 36 which is filled with fluid 18, heating mechanism 26 for heating fluid 18, a refrigerator mechanism 28 for cooling fluid 18, a fluid supply 30 for filling the bed or seat 36, a flow mechanism 32 for moving the fluid 18 through the bed or seat 36 and the heating mechanism 26 and the cooling mechanism 12, and a fluid thermometer 34 for measuring the temperature of the fluid 18. See figure 3. Alternatively, the cooling mechanism 12 includes a fluid suit 38 which is adapted to fit the individual. The suit 38 is filled with fluid 18. The cooling mechanism 12 includes a heating mechanism 26 for heating fluid 18, a refrigerator mechanism 28 for cooling fluid 18, a fluid 18 supply 30 for filling the suit 38, a flow mechanism 32 for moving the fluid 18 through the suit 38 and the heating mechanism 26 and the cooling mechanism 12, and a fluid thermometer 34 for measuring the temperature of the fluid 18, as shown in FIG. 4. Alternatively, the cooling mechanism 12 includes a fluid tunnel 40 through which fluid 18 is blown, as shown in FIG. 5, and in which the individual is disposed. The cooling mechanism 12 includes a heating mechanism 26 for heating fluid 18, a refrigerator mechanism 28 for cooling fluid 18, a fluid supply 30 for tunnel 40, a flow mechanism 32 for moving the fluid 18 through the tunnel 40 and the heating mechanism 26 and the cooling mechanism 12, and a fluid thermometer 34 for measuring the temperature of the fluid 18. Preferably, the fluid 18 includes a water mist.

The present invention pertains to a method for burning calories in an individual. The method comprises the steps of applying a fluid 18 in regard to the individual. Then there is the step of cooling the individual at the controlled rate with the fluid 18.

Preferably, before the cooling step, there is the step of placing a thermometer 16 with the individual to monitor the temperature of the individual. Before the applying step, there is preferably the step of monitoring the temperature of the fluid 18. Preferably, the applying step includes the step of causing the fluid 18 temperature to be greater than 78 and preferably 85 degrees Fahrenheit when the fluid 18 is initially applied to the individual and the cooling step includes the step of reducing gradually the temperature of the fluid 18 to below 68 degrees Fahrenheit. Before the cooling step, there is the step of raising the temperature of the fluid 18 to make the individual comfortable, before the step of reducing gradually the temperature of the fluid 18.

In the operation of the preferred embodiment, an individual who desires to burn calories to lose weight puts on a bathing suit 38 and enters the tub 24 of a Jacuzzi 22. See FIG. 2. The Jacuzzi 22 is filled with water at a temperature of about 88 degrees Fahrenheit. When the individual enters and settles into the Jacuzzi 22, there is enough water in the tub 24 to immerse the individual up to the individual's neck.

The controlling mechanism 14, such as a computer, of the Jacuzzi 22 is then turned on which begins the sequence to cause accelerated calorie burning of the individual. The controlling mechanism 14 turns on the flow mechanism 32 which includes a pump and jets in the tub 24 to cause water to circulate in the tub 24, and a fluid draw to obtain fluid 18 from the tub 24, as is well known in existing Jacuzzies. The computer mechanism also activates the heating mechanism 26 through which the water passes as it is moved by the flow mechanism 32 to heat the water. The water is first heated to an even higher temperature, such as 102 degrees Fahrenheit, to cause the capillaries of the individual to expand, as is a typical reaction when the body is overheated, to cool the body. In essence, this is tricking the body to make the body more susceptible to quick cooling to reach the shivering state, as is discussed below. The water temperature is raised to 102 degrees Fahrenheit in about 4 minutes and then maintained at this temperature for about another 2 minutes.

Next, the temperature of water is gradually reduced to about 63 degrees Fahrenheit. This is accomplished by the controller mechanism turning off the heating mechanism 26 and turning on the refrigerator mechanism 28 which cools the water in the tub 24. The refrigerator mechanism 28 is a common cooling system used to cool water that passes through it under the operation of the flow mechanism 32. If desired, to supplement the speed in which the water is cooled, a fluid supply 30 having already pre-cooled water, can be introduced until the tub 24 through the flow mechanism 32, which also directs an equal amount of water out of the tub 24 to a reservoir so the tub 24 will not overflow. The time it takes to reduce the water temperature to 63 degrees is about 7–10 minutes. The change in temperature should be gradual enough that it does not cause the individual any discomfort or feeling of sudden cold. As long as the change in temperature is gradual enough, the individual should feel no discomfort because of the coldness of the water.

Once the water temperature reaches 63 degrees Fahrenheit, the refrigerator mechanism 28 is turned off, but the flow mechanism 32 is maintained on. By maintaining the flow mechanism 32 on, a constant flow of water is moved across the body of the individual to ensure that the temperature of the water in contact with the surface of the body of the individual is essentially 63 degrees Fahrenheit. If the flow was stopped, the water immediately about the body of the individual could be heated from the body heat of the individual, and thus prolong the visit of the individual for the calorie reduction treatment.

Throughout the operation of the therapy, the water temperature of the water in the tub 24 is monitored by a fluid thermometer 34, which feeds back the temperature information to the controlling mechanism 14 so preset temperatures, such as 102 degrees Fahrenheit or 63 degrees Fahrenheit are not exceeded as the water temperature is increased, or decreased, respectively. A thermometer 16 attached to the ear of the individual and the computer also monitors the temperature of the individual to insure that the temperature of the individual is not reduced to a dangerous level. If the temperature of the individual is reduced to a dangerous level, then an alarm will sound for a technician who is at a remote monitor, monitoring the therapy, to go to the individual and make sure the individual leaves the tub 24. As a precaution, the heating mechanism 26 can be activated two minutes after the dangerous level of temperature of the individual is reached, as a safety precaution.

Figure 6:
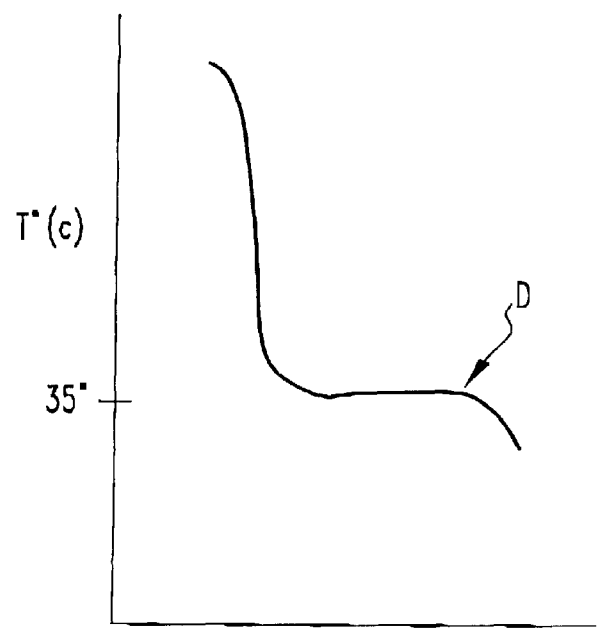
FIG. 6 is a graph of an individual's temperature over time subject to cooling.

Ideally, the reduction of temperature to 63 degrees Fahrenheit is of a temperature that is not uncomfortable to the individual, but will cause significant heat loss to the individual to cause the individual to begin shivering. In terms of physiological response, when the person begins to shiver, the temperature of the individual will reach a plateau, as shown in FIG. 6, and remain at that temperature while the individual burns calories to produce heat to maintain the temperature of the individual. A dangerous level D of temperature is reached when the temperature of the individual starts to fall again from that plateau. Thus, during the therapy, it is desired to reach the shivering state as quickly and as comfortably as possible, maintain the shivering state for about seven minutes, so that the plateau edge will not be reached, and then have the individual step out of the top and warm themselves naturally, without any heat other than body heat produced by the burning of calories of the individual being used to warm the individual. It has been determined that the energy used to support the shivering state and produce increased body heat production, generally comes from fat reserves. The advantage of this therapy is that it is a way for an individual, without necessarily having to perform exercise to specifically burn fat calories, to reduce their fat in their body.

The preferred embodiment describes the essentials of the therapy for causing an individual to produce excess heat by the burning of calories. This similar therapy can be used with a suit 38 as shown in FIG. 3, where the suit 38 is inflatable with a fluid 18, or a water bed or seat 36 that is also inflatable with fluid 18, as shown in FIG. 4. The suit 38 is put on the individual, or the individual reclines on the bed or chair, and can be encased in the bed or seat 36 so there is fluid 18 all about the individual and held in the suit 38, bed or chair. The suit 38, bed or seat 36 can have a flow mechanism 32 connected to a heating mechanism 26 and a cooling mechanism 12, as described above, to attain the desired changes in water temperature as described above for the above described effects. The temperature of the fluid 18 and the temperature of the person would be monitored in a similar way as described above. Water is a desirable fluid since it is readily available, but certainly the other types of fluids could be used if desired.

In another embodiment, a water tunnel 40, as shown in FIG. 5, can be used where the individual enters the tunnel 40 and the fluid 18 that is used is either air heated or cooled to a desired temperature at a given time, or a water mist is used to attain the above-described results. The individual can either stand or sit in the tunnel 40 while the therapy occurs and the temperature of the individual is monitored. In this instance, fans could blow the air or the mist across the individual to attain the shivering state.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for burning calories of an individual comprising:
   a cooling mechanism adapted to cool the individual's temperature by immersing the individual in fluid; and
   a controlling mechanism for controlling the rate at which the cooling mechanism cools the individual to cause the individual to shiver, the controlling mechanism includes a thermometer adapted to monitor the individual's temperature and an alarm which is sounded after the individual's temperature reaches a predetermined temperature.

2. An apparatus as described in claim 1 wherein the cooling mechanism includes a temperature mechanism for controlling the temperature of the fluid.

3. An apparatus as described in claim 2 wherein the temperature mechanism causes the cooling mechanism to bring the fluid temperature to be greater than 78 degrees Fahrenheit when the fluid is initially used for the individual and then causes the cooling mechanism gradually reduces the temperature of the fluid to below 68 degrees Fahrenheit, the temperature mechanism causes the cooling mechanism to raise the temperature of the fluid to heat the individual before causing the cooling mechanism to gradually reduce the temperature of the fluid, the cooling mechanism includes a Jacuzzi connected to the controlling mechanism having a tub, heating mechanism for heating fluid, a refrigerator mechanism for cooling fluid, a fluid supply for filling the tub, a flow mechanism for moving the fluid through the tub and the heating mechanism and the cooling mechanism, and a fluid thermometer for measuring the temperature of the fluid.

4. An apparatus has described in claim 2 wherein the temperature mechanism causes the cooling mechanism to bring the fluid temperature to be greater than 78 degrees Fahrenheit when the fluid is initially used for the individual and then causes the cooling mechanism gradually reduces the temperature of the fluid to below 68 degrees Fahrenheit, the temperature mechanism causes the cooling mechanism to raise the temperature of the fluid to heat the individual before causing the cooling mechanism to gradually reduce the temperature of the fluid, the cooling mechanism includes a fluid bed or seat which is filled with fluid, a heating mechanism for heating fluid, a refrigerator mechanism for cooling fluid, a fluid supply for filling the bed or seat, a flow mechanism for moving the fluid through the bed or seat and the heating mechanism and the cooling mechanism, and a fluid thermometer for measuring the temperature of the fluid.

5. An apparatus as described in claim 2 wherein the temperature mechanism causes the cooling mechanism to bring the fluid temperature to be greater than 78 degrees Fahrenheit when the fluid is initially used for the individual and then causes the cooling mechanism gradually reduces the temperature of the fluid to below 68 degrees Fahrenheit, the temperature mechanism causes the cooling mechanism to raise the temperature of the fluid to heat the individual before causing the cooling mechanism to gradually reduce the temperature of the fluid, the cooling mechanism includes a fluid suit which is adapted to fit the individual, said suit filled with fluid, said cooling mechanism includes a heating mechanism for heating fluid, a refrigerator mechanism for cooling fluid, a fluid supply for filling the suit, a flow mechanism for moving the fluid through the suit and the heating mechanism and the cooling mechanism, and a fluid thermometer for measuring the temperature of the fluid.

6. An apparatus as described in claim 2 wherein the temperature mechanism causes the cooling mechanism to bring the fluid temperature to be greater than 78 degrees Fahrenheit when the fluid is initially used for the individual and then causes the cooling mechanism gradually reduces the temperature of the fluid to below 68 degrees Fahrenheit, the temperature mechanism causes the cooling mechanism to raise the temperature of the fluid to heat the individual before causing the cooling mechanism to gradually reduce the temperature of the fluid, the cooling mechanism including a fluid tunnel through which fluid is blown and in which the individual is adapted to be disposed, said cooling mechanism includes a heating mechanism for heating fluid, a refrigerator mechanism for cooling fluid, a fluid supply for tunnel, a flow mechanism for moving the fluid through the tunnel and the heating mechanism and the cooling mechanism, and a fluid thermometer for measuring the temperature of the fluid.

7. An apparatus as described in claim 6 wherein the fluid includes a water mist.

8. An apparatus as described in claim 2, wherein the temperature mechanism causes the cooling mechanism to bring the fluid temperature to be greater than 78 degrees Fahrenheit when the fluid is initially used for the individual and then causes the cooling mechanism gradually reduces the temperature of the fluid to below 68 degrees Fahrenheit, the temperature mechanism causes the cooling mechanism to raise the temperature of the fluid to heat the individual before causing the cooling mechanism to gradually reduce the temperature of the fluid, the thermometer is adapted to attach to the ear of the individual.

9. A method for burning calories in an individual comprising the steps of:
   immersing the individual in a body of fluid; and
   cooling the individual at the controlled rate with the fluid.

10. A method as described in claim 9 wherein before the cooling step, there is the step of placing a thermometer in contact with the individual to monitor the temperature of the individual.

11. A method as described in claim 10 wherein before the immersing step, there is the step of monitoring the temperature of the fluid.

12. A method has described in claim 11 wherein the immersing step includes the step of causing the fluid temperature to be greater than 78 degrees Fahrenheit when the fluid is initially applied to the individual and the cooling step includes the step of reducing gradually the temperature of the fluid to below 68 degrees Fahrenheit.

13. A method as described in claim 12 wherein before the cooling step, there is the step of raising the temperature of the fluid to heat the individual before reducing gradually the temperature of the fluid.

14. A method as described in claim 13 wherein the cooling step includes the step of cooling the individual at the controlled rate with the fluid to cause the individual to shiver.

15. A method as described in claim 14 wherein the immersing step includes the step of flowing the fluid across the body of the individual.

16. A method as described in claim 9 wherein the cooling step includes the step of cooling the individual at the controlled rate with the fluid to cause the individual to shiver.

17. A method as described in claim 16 wherein the immersing step includes the step of flowing the fluid across the body of the individual.

18. A method as described in claim 9 including the step of the individual putting on a fluid suit; and wherein the immersing step includes the step of introducing the fluid into the suit.

19. A method for burning calories in an individual comprising the steps of:

blowing fluid across the individual; and cooling the individual at the controlled rate with the fluid.

20. A method as described in claim 19 wherein before the cooling step, there is the step of placing a thermometer in contact with the individual to monitor the temperature of the individual.

21. A method as described in claim 20 wherein before the blowing step, there is the step of monitoring the temperature of the fluid.

22. A method has described in claim 21 wherein the blowing step includes the step of causing the fluid temperature to be greater than 78 degrees Fahrenheit when the fluid is initially applied to the individual and the cooling step includes the step of reducing gradually the temperature of the fluid to below 68 degrees Fahrenheit.

23. A method as described in claim 22 wherein before the cooling step, there is the step of raising the temperature of the fluid to heat the individual before reducing gradually the temperature of the fluid.

24. An apparatus for burning calories of an individual comprising:

a cooling mechanism adapted to cool the individual's temperature by immersing the individual in fluid, the cooling mechanism includes a fluid for cooling the individual, the cooling mechanism includes a temperature mechanism for controlling the temperature of the fluid, the temperature mechanism causes the cooling mechanism to bring the fluid temperature to be greater than 78 degrees Fahrenheit when the fluid is initially used for the individual and then causes the cooling mechanism gradually reduces the temperature of the fluid to below 68 degrees Fahrenheit, the temperature mechanism causes the cooling mechanism to raise the temperature of the fluid to heat the individual before causing the cooling mechanism to gradually reduce the temperature of the fluid, the cooling mechanism includes a Jacuzzi connected to the controlling mechanism having a tub, heating mechanism for heating fluid, a refrigerator mechanism for cooling fluid, a fluid supply for filling the tub, a flow mechanism for moving the fluid through the tub and the heating mechanism and the cooling mechanism, and a fluid thermometer for measuring the temperature of the fluid; and a controlling mechanism for controlling the rate at which the cooling mechanism cools the individual to cause the individual to shiver, the controlling mechanism includes a thermometer adapted to monitor the individual's temperature and an alarm which is sounded after the individual's temperature reaches a predetermined temperature.

25. An apparatus for burning calories of an individual comprising:

a cooling mechanism adapted to cool the individual's temperature by immersing the individual in fluid, the cooling mechanism includes a fluid for cooling the individual, the cooling mechanism includes a temperature mechanism for controlling the temperature of the fluid, the temperature mechanism causes the cooling mechanism to bring the fluid temperature to be greater than 78 degrees Fahrenheit when the fluid is initially used for the individual and then causes the cooling mechanism gradually reduces the temperature of the fluid to below 68 degrees Fahrenheit, the temperature mechanism causes the cooling mechanism to raise the temperature of the fluid to heat the individual before causing the cooling mechanism to gradually reduce the temperature of the fluid, the thermometer is adapted to attach to the ear of the individual; and a controlling mechanism for controlling the rate at which the cooling mechanism cools the individual to cause the individual to shiver, the controlling mechanism includes a thermometer adapted to monitor the individual's temperature and an alarm which is sounded after the individual's temperature reaches a predetermined temperature.

26. An apparatus for burning calories of an individual comprising:

a cooling mechanism adapted to cool the individual's temperature by immersing the individual in fluid, the cooling mechanism includes a fluid for cooling the individual, the cooling mechanism includes a temperature mechanism for controlling the temperature of the fluid, the temperature mechanism causes the cooling mechanism to bring the fluid temperature to be greater than 78 degrees Fahrenheit when the fluid is initially used for the individual and then causes the cooling mechanism gradually reduces the temperature of the fluid to below 68 degrees Fahrenheit, the temperature mechanism causes the cooling mechanism to raise the temperature of the fluid to heat the individual before causing the cooling mechanism to gradually reduce the temperature of the fluid, the cooling mechanism including a fluid tunnel through which fluid is blown and in which the individual is disposed, said cooling mechanism includes a heating mechanism for heating fluid, a refrigerator mechanism for cooling fluid, a fluid supply for tunnel, a flow mechanism for moving the fluid through the tunnel and the heating mechanism and the cooling mechanism, and a fluid thermometer for measuring the temperature of the fluid, the fluid includes a water mist; and a controlling mechanism for controlling the rate at which the cooling mechanism cools the individual to cause the individual to shiver, the controlling mechanism includes a thermometer adapted to monitor the individual's temperature and an alarm which is sounded after the individual's temperature reaches a predetermined temperature.

* * * * *